United States Patent [19]
Bruce et al.

[11] Patent Number: 4,904,267
[45] Date of Patent: Feb. 27, 1990

[54] METHOD AND DEVICE FOR FIXING A JOINT PROSTHESIS

[75] Inventors: Lars M. Bruce; Ingrid E. Bruce, both of Viken, Sweden

[73] Assignee: AB Idea, Sweden

[21] Appl. No.: 876,870

[22] PCT Filed: Oct. 9, 1984

[86] PCT No.: PCT/SE84/00332
§ 371 Date: Jun. 5, 1986
§ 102(e) Date: Jun. 5, 1986

[87] PCT Pub. No.: WO86/02260
PCT Pub. Date: Apr. 24, 1986

[51] Int. Cl.⁴ ............................. A61F 2/32; A61F 2/30
[52] U.S. Cl. ........................................ 623/23; 623/16; 623/18; 623/66
[58] Field of Search ................ 623/12, 16, 18, 20, 623/22, 23

[56] References Cited

U.S. PATENT DOCUMENTS

| | | | |
|---|---|---|---|
| 3,987,499 | 10/1976 | Scharbach et al. | 623/18 |
| 4,011,602 | 3/1977 | Rubicki et al. | 623/18 |
| 4,177,524 | 12/1979 | Grell et al. | 623/18 |
| 4,495,664 | 1/1985 | Blanquaert | 623/23 |

FOREIGN PATENT DOCUMENTS

| | | | |
|---|---|---|---|
| 0006414 | 1/1979 | European Pat. Off. | |
| 0013863 | 1/1979 | European Pat. Off. | |
| 0022308 | 1/1981 | European Pat. Off. | 623/23 |
| 2502884 | 7/1976 | Fed. Rep. of Germany | |
| 2733826 | 2/1979 | Fed. Rep. of Germany | 623/23 |
| 8304387.7 | 8/1983 | Sweden | |

Primary Examiner—Richard J. Apley
Assistant Examiner—David J. Isabella
Attorney, Agent, or Firm—Bacon & Thomas

[57] ABSTRACT

The invention comprises a method and a device for fixing a joint prosthesis (1, 2; 5) in which all surfaces intended for tissue contact consist of titanium or a titanium-based tissue-compatible metallic material. For safely anchoring the prosthesis in relation to the bone tissue, use is made of pointed fixing elements (3, 11,16) which from the side of the bone tissue that should be facing the prosthesis are driven into the bone tissue with their pointed portions, and which are anchored in cement (9) between the prosthesis and the bone tissue or directly to the prosthesis, such that a solid connection is established by the bone tissue growing onto the anchored pointed portions. For proper adjustment of the prosthetic joint cup and the prosthetic joint ball, these members are moulded under pressure and heat, each respective articular surface being shaped against a model mould of the mating articular surface, and are hardened or sintered in shape contact for minimizing any aftertreatment.

18 Claims, 1 Drawing Sheet

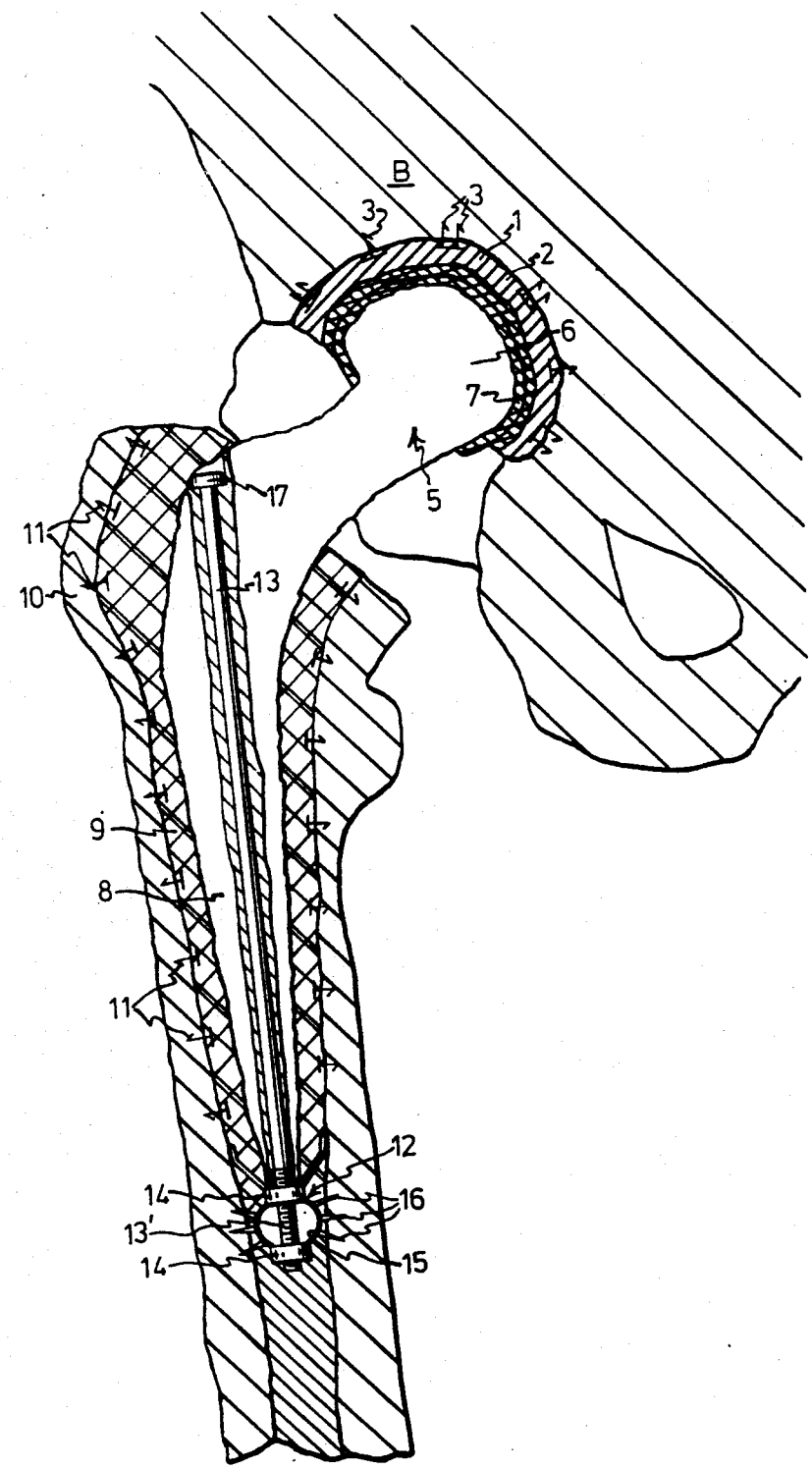

METHOD AND DEVICE FOR FIXING A JOINT PROSTHESIS

BACKGROUND OF THE INVENTION

1. Technical Field of the Invention

The present invention relates to a device for promoting the connection and fixing of joint prostheses, in particular hip joint prostheses but also shoulder, knee, foot and finger joint prostheses etc.

2. Description of Prior Art Practices

The implantation of joint prostheses is today general routine within orthopedic surgery. The surgical technique generally faces surmountable difficulties. However, a serious problem, apart from infections and thrombosis, is that one or both of the prosthetic components may loosen. The most typical joint reconstruction is the so-called hip joint reconstruction. About 5,500 operations of this type were performed in Sweden in 1981 and the commonest reasons therefor is arthosis in the hip joint or joint injuries caused by bone fractures and malformations resulting from other causes, e.g. rheumatic affections.

The problems involved in hip joint reconstruction have been subjected to intensive studies over the last decades and were discussed, for example at the so-called Consensus conference in Stockholm on May 12–14, 1982. In a Consensus statement made by the Medical Research Council after the conference, it was recommended in hip joint arthroplasty to use a femoral part of metal and pelvic part of plastic, and in routine cases to use cement for fixing the prosthesis.

From other sources it appears that by "cement" is generally understood a polymer which is allowed to polymerize in situ. The polymerization temperature may vary according to the components used but often considerably exceeds 47° C. which is a limit for the temperature to which bone tissue can be exposed without any commencing injury to the tissue resulting in so-called membrane formation.

Many researchers (Rik Huiskis at the Orthopedic Institute of the University of Nijmegen, E. Morscher at the Institute of Orthopedic Surgery at the University of Basel and others) are of the opinion that the material for the femoral part of the prosthesis should be selected among stainless steel, cobalt-chromium alloys and titanium, and that plastic should be selected for the pelvic part of the prosthesis. This combination is advantageous in that it entails relatively low friction and is wear-resistant. The choice of material is dictated not only by the mechanical properties of the material but also by the requirement that the material should be biocompatible with the body tissues. The use of stainless steel has declined to an increasing extent, the major interest being today directed toward titanium, titanium alloys and cobalt-chromium alloys. Of the metals hitherto tested, titanium seems to be the most tissue-compatible and corrosion resistant, and it has the excellent property of being highly resistant to fatigue and is relatively flexible.

As material for the acetabular cup, researchers primarily recommend polyethylene, Delrin and methyl methacrylate. High-density polyethylene is extensively used for acetabular cups because of its excellent frictional and wear resistant properties in combination with the above-mentioned metals and in that fragments resulting from wear cause a minimum of irritation to the tissue. Delrin, which has lately come into use, is harder than polyethylene and would scarcely offer any advantages over polyethylene. Among other possible materials, mention may be made of ceramic materials with high tissue compatibility. Such materials resist corrosion but are considered unreliable in respect of mechanical properties and may cause irritation and infections by fragments loosening from the surfaces of the ceramic material.

For fixing the parts of the prosthesis, and in particular the prosthetic part in the femur, use is made of cement which serves to fill the entire space between the prosthesis and the inner side of the bone wall and to distribute the load over as large an area of the bone as possible. Cement materials hitherto used (plastic glues) ensure good adherence to metal but are inapt to establish a chemical bonding to bone tissue. The main function of the cement therefore is to form a stabilizing filling between the prosthesis and the bone.

Although the prosthetic materials for the acetabular cup and the femoral head with the stem have been thoroughly tested and give satisfactory results in respect of the friction produced between the prosthetic cup and the prosthetic head or ball, and although materials with suitable elastic properties may be selected, one serious problem remains, i.e. that micromovements occur between the wall of the femoral medullary canal and the stem of the femoral prosthetic part fixed therein because of the loads on the femoral joint head caused by the weight and the movement of the body and because the stem is not sufficiently stably fixed with respect to the bone tissue in the wall of the medullary canal. Such micromovements which will be most pronounced between the upper and lower ends of the stem too often result in that the stem loosens, thus necessitating reoperation.

SUMMARY OF THE INVENTION

The object of the present invention is to provide a system and a method which ensure safe and permanent anchorage of prosthetic parts of the above-indicated materials having good tissue-compatible and mechanical properties versus bone tissue without adding any undesirable properties.

A further object of the invention is to provide a simplified method for economic production of joint cup and joint head prostheses with perfectly mating articular surfaces of low friction and suitable elastic properties with respect to each other.

According to the invention, these objects have now been achieved by a device and a method having the features stated in the accompanying claims.

BRIEF DESCRIPTION OF THE FIGURE OF DRAWING

The invention will be described in greater detail hereinbelow with reference to the accompanying drawing which shows an acetabular cup prosthesis which is designed in accordance with the invention and fixed to the pelvis by fixing means and by a method for fixing prostheses according to the invention, and which, in longitudinal section, shows part of the femur with a prosthesis fixed in the femoral medullary canal and comprising a joint head or ball with a stem conformed to the acetabular cup of the joint.

DETAILED DESCRIPTION OF THE PREFERRED EMBODIMENT

The acetabular cup prosthesis shown in the drawing consists of a cup-shaped main portion 1 and a layer 2 applied to the concave side of the cup and forming the articular surface of the acetabular prosthesis. The main portion 1 of the acetabular prosthesis is preferably obtained by compression moulding a metal powder and sintering the metal powder according to known powder moulding, compression moulding and sintering methods, such that its concave side is provided with pores. However, it may also be possible to obtain the portion 1 from metal by a suitable cutting technique or a conventional metal shaping technique, such that the concave side is given an uneven structure corresponding to the above-mentioned pores and ensuring good adherence to the layer 2 when prepared as described below. A suitable material for the acetabular portion 1 is selected from any of the metals mentioned by way of introduction, preferably titanium which is known for its tissue compatibility, a tissue-compatible titanium alloy or optionally a cobalt-chromium alloy of any other tissue-compatible metallic material.

The cup portion 1 is preferably designed in such a manner that its convex upper face intended to engage the pelvis B is also porous or rough to increase the ability of ongrowth of the bone tissue to said surface.

The acetabular portion 1 can be fixed to the pelvis, for instance by means of pins or screws in a manner which is known in conjunction with the fixing of cup prostheses of plastic, but the cup portion 1 is preferably fixed in accordance with the invention in such a manner that a plurality of pins 3 projecting from the convex side of the portion 1 and consisting of a tissue-compatible metal onto which living bone tissue can grow, are fixed in the material. These pins should have barbs and pointed ends, such that they can be driven into the underlying pelvic bone and mechanically hook onto the bone tissue so as to form a bond which will be subsequently strengthened by the bone growing onto the pins.

Before the acetabular portion 1 is connected to the pelvic bone, the layer 2 is preferably applied according to the invention in such a manner that the cup portion 1 is placed in an injection moulding tool by means of which the layer 2 is injection moulded against a model of the joint ball so as to obtain a good calibration of the articular surface of the joint cup with respect to a joint ball with which it is to cooperate. A suitable material for the layer 2 is preferably selected among any of the initially mentioned plastics or any other tissue-compatible plastic with suitable elasticity and thickness for distributing the loads which generally occur in a hip joint. Suitable plastics are for example plastics of the types polyethylene, Delrin and methyl methacrylate. Instead of plastic, it is possible to choose a suitable enamel or a ceramic material.

The femoral prosthetic part 5 is preferably prepared in the same way and from the same types of material as the acetabular prosthetic portion 1. By preparing the prosthetic part 5 by moulding, compressing and sintering a metal powder of a suitable particle size, it is possible to obtain an appropriately porous or rough surface to be connected to cement of the type which is generally used for fixing prosthetic stems in the medullary canal of a bone. However, the femoral prosthetic part may also be produced in a conventional way. In this case, too, the surface of the stem portion should be sufficiently porous or rough for adequate adherence to the cement material selected for applying in the medullary canal of the bone.

When the prosthetic part 5 has been prepared, it is inserted in an injection moulding tool by means of which there is applied to the joint ball 6 a layer 7 of a material which gives a uniform, smooth articular surface similar to the articular surface of the, acetabular prosthesis 1, 2. The injection-moulded material on the joint ball is selected with regard to the injection-moulded material on the joint cup or socket so as to obtain the best possible combination in respect of both friction and elasticity between the joint socket and the joint ball, for instance plastic to plastic, enamel to plastic or ceramic to plastic. By injection moulding the layer 7 on a model of the joint socket and vice versa, it is possible to obtain a very accurate fit between socket and ball. By this moulding technique for both the joint ball and the joint socket, the very expensive finishing and polishing operations hitherto used may be reduced or entirely dispensed with.

However, for the combination of articular surfaces of the type metal to plastic it is also possible to apply a metallic surface to the joint ball by metal evaporation in vacuum or, possibly, by electrolytic or electrochemical metal deposition. However, these methods generally necessitate the use of more precise manufacturing methods for the joint ball surface to which the layer 7 should be applied, because it is more difficult to achieve the required exact calibration of shapes and dimensions by plating or metal deposition than by injection moulding of an injection mouldable material. It should be emphasized that a substantial advantage of the manufacturing method according to the invention is that it makes it possible to reduce the demand for accuracy in the manufacture of the prosthetic parts on which the articular surfaces are to be designed by applying a layer of material.

As appears from the above, the acetabular cup. prosthesis is fixed to the pelvic bone without the use of cement. For fixing the stem 8 of the prosthetic part 5 in the femoral medullary canal, use is however made of the well-tried technique of embedding the stem in cement 9 filling the entire space between the stem 8 and the wall 10 of the bone. As appears from the introduction to the specification, this method does however not give a fully satisfactory result because the cement may loosen from the bone tissue. Therefore, the application of cement is supplemented according to the invention by fixing the cement material to the bone tissue by means of elements of a metallic material which is tissue-compatible and allows the bone tissue to grow onto the elements and which is "cement-compatible", such that the conventional cement material used will adhere to the elements.

In accordance with the invention, the metallic fixing elements used are preferably barbed pins 11 similar to the pins 3 which are used for fixing the joint cup to the pelvic bone. The barbed pins 11 can be applied to the bone tissue, for instance by driving them into the bone tissue from the inner side of the medullary canal by means of a driving tool or by pressing them into the bone tissue by means of any suitable tool. The pins are fixed in place before the stem of the femoral prosthetic part is inserted and cemented in the medullary canal of the bone. The pins should only penetrate into the bone tissue and should of course not project from the outer side of the wall of the bone. On the other hand, the pins should have, at the inner side of the medullary canal, sufficiently large contact surfaces, contact heads or projections to offer an adequate attachment surface for the cement material.

Instead of barbed pins, which are preferred, use may be made of metal screws which may optionally be screwed from the outside so as to extend into the medullary canal of the bone to be enclosed therein and bonded to the cement material.

As an alternative of more or less sophisticated pins, use may be made of metal plates or strips which are provided with pins and to which the cement material to be used for cementing the prosthetic stem adheres.

It may be advantageous to use pins, screws or the like having porous surfaces for good adherence to the cement material and for stable ongrowth of the bone tissue to the pins, screws etc.

It is advantageous to design the metal elements 11 in such a manner that the cement material 9 not only adheres to the metal elements but also will be firmly connected, because of the shape of such elements, by embedding portions thereof. A sufficient number of relatively small pins, screws etc. should be used, especially in the region of the lower end and neck portion of the prosthetic stem, such that there will be a sufficient number of fixing points to efficiently secure the cement to the wall of the bone.

By using a certain concentration of pins, nails etc. in annular areas in the upper portion of the medullary canal of the bone adjacent the joint ball and at the lower end of the prosthetic stem, it is possible in these areas to obtain concentrated anchorage, and the use of a centering ring of metal which, according to conventional methods, is often mounted on the stem, especially at the lower end thereof, may be dispensed with.

The number of such fixing points should however be selected also in consideration of the risk that a reoperation may become necessary despite the reliable fixing. In a reoperation, the fixing points must of course be loosened to make it possible to remove the prosthesis, which speaks for as few fixing points as possible. For loosening the pins in connection with a reoperation, it may become necessary, from the outside, to bore or otherwise break loose the attachments. The loosening of the fixing points will of course become easier, the fewer the fixing points are. If the pins are bored loose, the holes which are left open will be so small that they will be fully healed by growth of bone tissue after a reoperation.

As already intimated above, use is often made of a guide or centering means at the outer (lower) end of the stem of the femoral prosthesis to maintain the stem in as correct a position as possible during the cementing operation. In a per se known embodiment, the centering means consists of a band-shaped ring disposed on the stem adjacent its lower end and being of the same material as the stem. The ring generally carries a sparse corona of obliquely outwardly-upwardly directed resilient tongues or tines of the same material which are urged by the wall of the bone inwardly towards the prosthetic stem during the insertion thereof in the medullary canal. The ring with its resilient tongues or tines are capable but to an insignificant extent to prevent the loads on the femoral prosthesis from initiating a vibratory and oscillatory movement of the stem in the medullary canal. Such an oscillatory movement, which may initially be microscopically small and has its amplitude at the lower end of the stem, tends to increase with time and may in a relatively short time have a devastating consequence for the retention of the femoral prosthesis.

To pursue the idea of stabilizing the prosthesis in the femoral medullary canal, it is therefore suggested according to the invention that a guide or centering means, at least at the lower end of the prosthetic stem, is fixed by means of hooks, pins or the like which penetrate the wall of the bone and consist of titanium or a titanium-based tissue-compatible material allowing the bone tissue to grow onto the pins or the like.

There are many different ways for achieving such a penetration of pins or like elements for ongrowth of bone tissue, which are fixed or being fixed to a guide or centering means of the above type or simply to the prosthetic stem itself, One way is implanting pins from the outside in the wall of the bone and fixing the pins to the stem. Another way is fixing a ring by means of pins or a circle of pins in the bone prior to the insertion of the prosthesis, such that the prosthetic stem can thereafter be inserted in the ring or circle of pins with adequate fit therein for stable retention with or without the use of cement. Another possible way according to the invention, which seems promising but has not yet been clinically verified, is using a pin-equipped, expandable annular member 12 which is expandable from the outside and, for example, is of the schematic design intimated in the drawing.

The illustrated annular member 12 is expandable by means of a bolt 13 which with a threaded end portion 13' engages in two internally threaded expansion washers 14 on either side of an expandable annular torus 15 which is mounted at the end portion of the stem 8 and from which a number of pins project radially outwardly, so that they can be urged into the femoral wall 10 by rotation of the bolt 13. The bolt extends through a channel bored in the stem 8 to a point at the upper end portion of the stem that is spaced apart and laterally offset from the joint ball 6. At its upper end, the bolt 13 has a member 17 with which a tool (not shown) can engage.

For moving the expansion washers 14 towards each other for expanding the member 15, one washer has a left-hand thread and the other a right-hand thread, and the thread of the bolt consists of one left-hand threaded portion and one right-hand threaded portion, i.e. the washers 14 and the bolt 13 act as a turnbuckle device in the illustrated example.

Instead of the expansion assembly 12 shown in the drawing, it is possible to use any other per se known expandable device suitable for the contemplated purpose, provided it can properly stabilize the stem 8 in the above-described manner by expanding, such that the pins will penetrate into the femoral wall, and/or by expanding into engagement with and abutment against the inner side of the wall.

The toroid member 15 should consist of a tissue-compatible material, such as titanium or a titanium-based material or a tissue-compatible plastic. It is possible by a suitable choice of material and design to achieve a certain elasticity to force the expandable member 12 (15) to conform to the shape of the medullary canal without neglecting the need for eliminating vibrations or at east reducing them in the prosthetic stem in the femoral medullary canal.

It should be noted in particular that the expandable annular member and the prosthetic stem can be so arranged that the stem can be inserted in the annular member after expansion thereof in the medullary canal before the prosthesis is inserted in place. In this case, the prosthetic stem need not have a bore and the bolt 13 may be dispensed with, but there will instead be required a tool which can be inserted through the bone or at the end of the medullary canal for expanding said member.

It should be noted that the invention is only schematically illustrated in the drawing, in which for instance the thickness of the cement layer 9 and of the layers 2 and 7 forming articular surfaces is chosen rather for purposes of illustration, which also applies to the pins serving as fixing elements.

The thickness of the different layers and in particular the geometrical shapes of the fixing elements may vary and several modifications of the shape of the fixing elements are possible within the scope of the invention. Also, it is possible to use many combinations of materials for the fixing elements. Thus, it is possible, for instance, to make the fixing elements of steel or any other inexpensive material and to coat the surface with a more biocompatible material, primarily pure titanium or a titanium-based material which is particularly tissue-compatible and in other respects biologically acceptable.

It should however be emphasized that the femoral prosthesis need not consist of titanium in its entirety. On the contrary, an embodiment is preferred which consists of a core of for instance steel coated with a titanium metal. The different fixing elements of metal preferably consist of for instance steel with a titanium coating in accordance with the above. Further, it should be noted that the joint prosthesis of the invention can also be used for joints other than hip joints, for instance knee joints, shoulder joints etc., and that it is possible, as a supplement to the illustrated fixing elements, to use metal screws coated with a surface layer of titanium. Steel screws with a titanium layer provide the same tissue compatibility as titanium screws but are less expensive and, moreover, a suitable elasticity is more readily obtainable by a combination of steel/titanium surface layers. Incidentially, such screws may also be used for fixing bone shafts in cases of complicated fractures or for strengthening the bone shaft where a joint prosthesis is applied.

Nor is the invention restricted to the method described above where the metallic fixing elements are applied before the prosthetic stem 8 is cemented in the medullary canal. In fact, it is possible, from the outside, to drive or screw fixing elements through the wall of the bone and into the cement material. In order to obviate any impermissible stresses, use should then be made of fixing elements provided with throughholes allowing cement subjected to pressure to escape therethrough. This method of application can also be carried out after cementing but before the cement has set.

As a supplement to or in replacement of the above-mentioned bridging elements in the form of pins, staples, screws or the like between bone cement for fixing a prosthesis with respect to a bone tissue, and the bone tissue itself, the following means are suggested which for the sake of simplicity will be described in connection with a hip joint prosthesis with a stem to be connected to the femoral wall, but may also apply to many other cases where a prosthesis should be fixed to bone tissue, possibly also artificial roots or stems of teeth.

In the open medullary canal of the bone, titanium particles are inserted which are caused to adhere temporarily or more permanently to the bone tissue. The particle layer may be concentrated or relatively sparse depending on the field of use and on how concentrated points of attachment are desired. These particles or grains may be applied in any suitable manner, for instance advantageously by spraying through a nozzle. The particle size may in principle be selected within the range of from $\mu$m to several mm depending on the size of the prosthesis and the thickness of the bone cement layer. Thus, the titanium particles may also be in the form of a very fine power. This powder can be applied by means of fine nozzles before or after application of the prosthesis but before the application of the bone cement. However, it is quite possible and, in some cases, even advisable to mix the titanium powder or grains with the bone cement.

In tests on living animal bone tissues, it has been found that the bone tissue grows onto the grains fixed by means of the bone cement, whereby the cement which readily adheres to the prosthesis, as when pins etc. are used, will form a solid bridge between the bone tissue and the prosthesis.

The titanium grain or powder material can be applied in the form of a more or less easy flowing paste or thin slurry or, if a fine grained titanium powder is used, as a pigment-like substance.

Good results are also anticipated for a method according to the invention in which titanium grains are introduced as a layer between the prosthesis and the bone tissue, whereupon a binder for fixing the prosthesis and for fixing the grains is injected in the powder layer by means of an injection needle or in any other suitable way and in such an easy flowing state that the binder will fill the voids between the grains by capillary action.

In the case described above, animal tests have confirmed or given to expect very favourable results which should also apply to human application.

In combination with the fixing and consolidating methods described above, in which use is made of a binder of some kind or also simply bonding by sintering, it may also be possible to use fibres, such as titanium fibres, but also other fibres, such as carbon fibres, are conceivable.

We claim:

1. A method for fixing a prosthesis in relation to living bone tissue comprising applying between the prosthesis and the bone tissue and in contact with the bone tissue, a plurality of fixing elements of a material and a surface structure which allows bone tissue to grow thereon, wherein the fixing elements have a first end which is inserted into the bone and a second end with a contact head or projection thereon to provide an attachment surface for the bone cement; said fixing elements being inserted into the bone so that the projections or contact heads are spaced apart from the prosthesis and the bone and applying a bone cement which is capable of adhering to the prosthesis, between the bone tissue and the prosthesis, such that the prosthesis whereby the projections or contact heads are completely embedded in said bone cement through said bone cement and said elements, is connected to the bone tissue.

2. Method as claimed in claim 1, wherein each element to be fixed in contact with living bone tissue comprises a body having a coating disposed thereon for surface contact with the bone tissue said coating comprising a tissue-compatible material which permits ongrowth of bone tissue to the element, said coating being connected to the body so as to form a surface layer which is mechanically inseparable with respect to the body and which tightly encloses and covers at least the portion of the body which engages the bone tissue in the position of use of the element.

3. Method as claimed in claim 1 or 2, wherein said coating is a coating of a titanium-based or pure titanium.

4. Method as claimed in claim 1, wherein each element is an element with a body produced by moulding and sintering a sinterable material, such that the body or the portion thereof to which said coating is applied, has pores or other uneven portions, said coating covering said uneven portions, such that said uneven portions are reflected on the outer side of the coating.

5. Method as claimed in claim 1, wherein said elements are pointed or barbed fixing elements or are in the form of screws or pins with projections or heads at the ends opposite to those provided with said pointed portions, to be anchored in the bone cement between the prosthesis and the bone tissue.

6. Method as claimed in claim 5 wherein the pointed fixing elements are screws or pins comprising a body of a metallic material having a coating of a titanium-based metal or pure titanium applied by metal evaportion on a porous surface of said body.

7. Method as claimed in any one of claims 5 or 6, wherein some of said fixing elements are disposed on a supporting, expandable member and driven with the pointed portions into the bone tissue by expansion of the expandable member.

8. Method as claimed in claim 7 wherein said fixing elements comprise a powder or grains of titanium which are applied to the bone tissue and/or the bone cement such that, the titanium grains permit ongrowth of bone tissue to the grains and such that said grains are connected to the bone cement, whereby the bone tissue and the prosthesis are connected to each other.

9. Method as claimed in claim 7, wherein the titanium powder or grains are applied by spraying or painting.

10. Method as claimed in claim 7, wherein the titanium powder or grains are applied as a dispersion in the liquid.

11. Method as claimed in claim 8, wherein the titanium powder is applied in the form of a dispersion in a paste-forming substance in the form of a dispersion in a paste-forming substance compatible with bone cement.

12. Method as claimed in claim 8, wherein the titanium powder or grains are applied in contact with the bone tissue as a dispersed additive in the bone cement.

13. Method as claimed in claim 8, wherein other tissue-compatible fibres are applied in contact with the bone tissue as a layer disposed between the bone tissue and the prosthesis, and that the pores and other interspaces between the titanium grains and/or other fibres are filled with a liquid bone cement which is thereafter caused to set in contact with the prosthesis.

14. The method of claim 1, wherein the first end of the fixing element is pointed and said first end is barbed so that the barbs of the elements engage the bone when the first end is inserted into the bone.

15. The method of claim 14, wherein the fixing elements are in the form of screws or pins.

16. A method of fixing a hip joint prosthesis, said joint being of the type which comprises an acetabular cup prosthetic part and a femoral prosthetic part having a ball and stem; said method comprising:

fixing said acetabular cup into a pelvis by means of pins or screws which extend from a convex portion of the cup into the pelvic bone; said cup having an articular surface layer which is applied to a concave surface of the cup before said cup is fixed to the bone;

providing a plurality of fixing elements; said fixing elements having a first end for insertion into the bone tissue and a second end with a contact head or projection thereon;

inserting the first end of the fixing elements into the bone within a femoral medullary canal; said elements being inserted into the bone so that the projections or contact heads are spaced apart from the bone;

inserting the stem section of the femoral prosthetic part into the femoral medullary canal containing said fixing elements; said stem having a centering means attached at a lower end thereof and said centering means having penetrating means for penetrating the wall of the bone to fix said centering means in the femoral medullary canal; and said stem being narrower than the medullary canal so that upon insertion, a space is formed between the stem and the bone whereby said projections or said contact heads are spaced apart from the stem and the bone;

inserting said penetrating means into the bone to fix the centering means and attached stem to the bone;

cementing the stem in a canal by filling the space between the stem and the bone with bone cement whereby said femoral prosthetic part becomes fixed in the femoral medullary canal.

17. The method of claim 16, wherein the centering means comprises an expandable annular member expandable by means of a threaded bolt extending through a channel; said channel extending from a top portion of the step to the centering means attached to the lower end of the stem; said thread of the bolt consisting of one left-hand threaded portion and one right-hand threaded portion and said bolt engaging two internally threaded annular expansion washers on either side of an expandable annular torus of the centering means which is mounted at the end portion of the stem and from which a plurality of pins project radially outwardly to engage the bone; one of said washers having right-hand thread and the other having left-hand thread so that the washers and bolt cooperate as a turnbuckle when the bolt is turned to cause the washers to move towards one another and thereby causing expansion of the annular torus and penetration of the pins into the bone;

said method further comprising the step of turning the bolt to cause penetration of the pins extending from the torus into the bone.

18. The method of claim 16, wherein the fixing elements are barbed pins and said method includes the step of inserting said barbed pins into the bone.

* * * * *